United States Patent [19]

Hotomi et al.

[11] Patent Number: 5,919,291
[45] Date of Patent: *Jul. 6, 1999

[54] AQUEOUS RECORDING SOLUTION FOR INK JET

[75] Inventors: Hideo Hotomi, Nishinomiya; Takamasa Ueda, Ibaraki, both of Japan

[73] Assignee: Minolta Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/833,822

[22] Filed: Apr. 9, 1997

[30] Foreign Application Priority Data

Apr. 10, 1996 [JP] Japan ................................. 8-113102
Jun. 21, 1996 [JP] Japan ................................. 8-181255

[51] Int. Cl.$^6$ .......................... C09D 11/00; A01N 65/00
[52] U.S. Cl. ........................ 106/15.05; 106/31.27; 106/31.36; 106/31.37; 106/31.43; 106/31.6; 106/31.68; 106/31.69; 106/31.75; 424/78.09; 424/195.1; 424/722
[58] Field of Search .................. 106/15.05, 31.27, 106/31.36, 31.37, 31.43, 31.6, 31.68, 31.69, 31.75; 424/78.09, 195.1, 722

[56] References Cited

U.S. PATENT DOCUMENTS

| | | | |
|---|---|---|---|
| 4,581,071 | 4/1986 | Akutsu et al. | 106/31.43 |
| 5,017,228 | 5/1991 | Goda | 106/31.34 |

FOREIGN PATENT DOCUMENTS

| | | | |
|---|---|---|---|
| 58-134164 | 8/1983 | Japan | 106/31.27 |
| 62-34350 | 7/1987 | Japan . | |
| 2-12266 | 3/1990 | Japan . | |

OTHER PUBLICATIONS

Chemical Abstract No. 68:21177 which is an abstract of Austrian Patent Specification No. 263,403 (Nov. 1965).

Chemical Abstract No. 89:141102 which is an abstract of an article by Fujita et al entitled "Effect of leave extracts of Aloe . . . ", Antimicrob. Agents Chemother (1978) 14(1), 132–6. No month.

Chemical Abstract No. 96:99422 which is an abstract of Japanese Patent Specification No. 56–161311 (Dec. 1981).

Chemical Abstract No. 109:187346 which is an abstract of an article by Schmid et al entitled "Distribution . . . In Malvaceous Plant Parts", Phytochemistry (1988) 27(9), 2831–4. No month.

WPIDS Abstract No. 66–09456F which is an abstract of Australian Patent Specification No. 6102585 (Aug. 1963).

WPIDS Abstract No. 68:21177 which is an abstract of Great Britain Patent Specification No. 2,245,143 (Jan. 1992).

JAPIO Patent Abstract No. JP355043153A which is an abstract of Japanese Patent Specification No. 55–043153 (Mar. 1980).

JAPIO Patent Abstract No. JP360199077A which is an abstract of Japanese Patent Specification No. 60–199077 (Oct. 1985).

JAPIO Patent Abstract No. JP360199078A which is an abstract of Japanese Patent Specification No. 60–199078 (Oct. 1985).

JAPIO Patent Abstract No. JP360199079A which is an abstract of Japanese Patent Specification No. 60–199079 (Oct. 1985).

JAPIO Patent Abstract No. JP401271470A which is an abstract of Japanese Patent Specification No. 01–271470 (Oct. 1989).

JAPIO Patent Abstract No. JP404008777A which is an abstract of Japanese Patent Specification No. 04–008777 (Jan. 1992).

JAPIO Patent Abstract No. JP406049401A which is an abstract of Japanese Patent Specification No. 06–049401 (Feb. 1994).

*Primary Examiner*—Anthony Green
*Attorney, Agent, or Firm*—McDermott, Will & Emery

[57] ABSTRACT

An aqueous recording solution for ink jet according to the present invention contains at least a water-soluble dye, a water-soluble fungusproofing agent and water, and a liquid extracted from at least one type of malvaceae, orchidaceae and aloe is used as the water-soluble fungusproofing agent.

23 Claims, No Drawings

AQUEOUS RECORDING SOLUTION FOR INK JET

BACKGROUND OF THE INVENTION

1. Field of the Invention

The present invention relates generally to an aqueous recording solution for ink jet used in an ink jet recorder such as an ink jet printer, and more particularly, to an aqueous recording solution for ink jet whose fungus resistance is improved without degrading the properties of an aqueous recording solution for ink jet.

2. Description of the Related Art

As a recording solution used in an ink jet recorder such as an ink jet printer, an oily recording solution and an aqueous recording solution have been conventionally used.

The aqueous recording solution for ink jet generally used does not necessarily have sufficient fungus resistance. If such an aqueous recording solution is used in an ink jet recorder, fungus is produced in the recording solution, whereby a solution passage and a nozzle in the recorder are clogged, and the color of the recording solution is changed by the action of the fungus.

In order to prevent the fungus from being produced in the aqueous recording solution used in the ink jet recorder, an aqueous ink for ink jet recording containing a water-soluble dye, a fungusproofing agent and water has been conventionally known, as disclosed in Japanese Patent Publication No. 34350/1987 and Japanese Patent Publication No. 12266/1990.

When fungusproofing agents such as Thiabendazole which is a fungusproofing agent of an imidazole system (manufactured by US Melk K.K.) or Melgal BCM (manufactured by Hoechst Japan Ltd.) described in the above-mentioned publications are used, there arises a problem in safety, and the properties of the recording solution are degraded, for example, because the fungusproofing agent is highly toxic if it has a high fungusproofing effect.

SUMMARY OF THE INVENTION

An object of the present invention is to solve the above-mentioned problems in an aqueous recording solution for ink jet used in an ink jet recorder such as an ink jet printer.

Specifically, the present invention provides, in the above-mentioned aqueous recording solution for ink jet, an aqueous recording solution for ink jet having superior fungus resistance and capable of carrying out stable ink jet recording by eliminating the possibilities that fungus is produced in the recording solution, so that a solution passage and a nozzle in an ink jet recorder are clogged, and the color of the recording solution is changed, and the possibilities that toxicity in the recording solution is increased so that there arises a problem in the safety thereof, and the properties of the recording solution are degraded, as in a case where a general fungusproofing agent is used.

In the present invention, in order to solve the above-mentioned problems, in an aqueous recording solution for ink jet containing at least a water-soluble dye, a water-soluble fungusproofing agent and water, a liquid extracted from at least one type of malvaceae, orchidaceae and aloe is used as the above-mentioned water-soluble fungusproofing agent.

Furthermore, in the present invention, in order to solve the above-mentioned problems, in an aqueous recording solution for ink jet containing at least a water-soluble dye, a water-soluble fungusproofing agent and water, alkali silicate indicated by the following general formula (1) is used as the above-mentioned water-soluble fungusproofing agent:

$$M_2O \cdot nSiO_2 \quad (1)$$

(In the formula, M indicates K or Na, and N indicates an integer of 1 to 4)

There and other objects, advantages and features of the invention will become apparent from the following description thereof taken in conjunction with the accompanying drawings which illustrate specific embodiments of the invention.

DESCRIPTION OF THE PREFERRED EMBODIMENTS

An aqueous recording solution for ink jet according to the present invention contains at least a water-soluble dye, a water-soluble fungusproofing agent and water.

A liquid extracted from at least one type of malvaceae, orchidaceae and aloe can be used as the water-soluble fungusproofing agent. In containing the water-soluble fungusproofing agent in the recording solution to give fungus resistance, when the above-mentioned liquid extracted from at least one type of malvaceae, orchidaceae and aloe is used, there are no possibilities that toxicity in the recording solution is increased so that there arises a problem in the safety thereof, and the properties of the recording solution are degraded, as in a case where a general fungusproofing agent is used, whereby fungus is sufficiently prevented from being produced in the recording solution. When the recording solution is used in an ink jet recorder, a solution passage and a nozzle in the recorder are not clogged, and the color of the recording solution is not changed, so that stable ink jet recording can be carried out. If the extracted liquid is added, the viscosity of the recording solution is increased, whereby the extracted liquid can be also utilized for modifying the viscosity of the recording solution. Examples of the above-mentioned malvaceae include eichhornia crassipes and hibiscus.

In a case where the liquid extracted from at least one type of malvaceae, orchidaceae and aloe is used as the water-soluble fungusproofing agent, in containing the extracted liquid in the recording solution, if the amount thereof is small, a sufficient fungusproofing effect is not obtained. On the other hand, if the amount thereof is too large, the drying characteristics or the like of the recording solution are degraded, resulting in degraded fixing properties of the recording solution to paper or the like. Therefore, it is preferable that the content of the extracted liquid in the recording solution is in the range of 0.01 to 5% by weight.

Furthermore, as the water-soluble fungusproofing agent, alkali silicate expressed by the following general formula (1) may be used:

$$M_2O \cdot nSiO_2 \quad (1)$$

(In the formula, M indicates K or Na, and n indicates an integer of 1 to 4)

In containing the water-soluble fungusproofing agent in the recording solution to give fungus resistance, when the above-mentioned alkali silicate is used, there are no possibilities that toxicity in the recording solution is increased so that there arises a problem in the safety thereof, and the properties of the recording solution are degraded, as in a case where a general fungusproofing agent is used, whereby fungus is sufficiently prevented from being produced in the recording solution. When the recording solution is used in the ink jet recorder, the solution passage and the nozzle in the recorder are not clogged, and the color of the recording solution is not changed, so that stable ink jet recording can be carried out.

Furthermore, in containing the above-mentioned alkali silicate in the recording solution as the water-soluble fungusproofing agent as described above, if the amount thereof is small, a sufficient fungusproofing effect is not obtained. On the other hand, if the amount thereof is too large, the drying characteristics or the like of the recording solution are degraded, resulting in degraded fixing properties of the recording solution to paper or the like. Therefore, it is preferable that the content of the alkali silicate in the recording solution is in the range of 0.01 to 10% by weight.

As a coloring agent used for the aqueous recording solution for ink jet according to the present invention, it is possible to use known coloring agents such as pigments, colored resin fine particles, oil-soluble dyes, and water-soluble dyes. Examples of the water-soluble dyes include acid dyes, direct dyes, basic dyes, and reactive dyes. The content of the coloring agent in the recording solution is 0.5 to 10% by weight, preferably 1 to 7% by weight, and more preferably 2 to 6% by weight.

Furthermore, the amount of water used as a solvent for the above-mentioned water-soluble fungusproofing agent and water-soluble dye in the recording solution is set to 50 to 90% by weight, and preferably 70 to 90% by weight.

In the aqueous recording solution for ink jet, a water-soluble organic solvent, a viscosity modifier, surface active agent, an amphipathic affinity agent, a pH adjustor, a chelating agent, or the like is added in order to improve the properties of the recording solution in addition to the water-soluble dye, the water-soluble fungusproofing agent and water. Further, an oxygen absorbent, a rust proofing agent, a quencher, or the like can be added as required.

In adding the water-soluble organic solvent to the recording solution, monohydroxy alcohol such as methyl alcohol, ethyl alcohol, n-propyl alcohol, or isopropyl alcohol is added in order to increase the drying characteristics of the recording solution to improve the fixing properties of the recording solution, polyalkylene glycol such as polyethylene glycol or polypropylene glycol, alkylene glycol whose alkylene group contains two to six carbon atoms such as ethylene glycol, propylene glycol, butylene glycol, or hexylene glycol, polyhydroxy alcohol such as glycerin or glycerol, or polyhydroxy alcohol ethers such as ethylene glycol methyl ether, ethylene glycol ethyl ether, diethylene glycol methyl ether, diethylene glycol ethyl ether, diethylene glycol butyl ether, or triethylene glycol butyl ether is added in order to improve moisture retention in the recording solution and modify the viscosity and the surface tension thereof, and cyclic amide such as 2-pyrrolidone or 1(N)-methyl-2-pyrrolidone can be used for the purpose of increasing the rust resistance and corrosion resistance of the recording liquid and preventing the nozzle or the like from being clogged.

In containing the water-soluble organic solvent in the recording solution, the content of the monohydroxy alcohol is not more than 10% by weight, the content of the polyhydroxy alcohol is 5 to 30% by weight and preferably 5 to 10% by weight, the content of polyhydroxy alcohol ether is 5 to 20% by weight and preferably 5 to 10% by weight, and the content of the cyclic amide is not more than 10% by weight and preferably not more than 2% by weight. The content of the whole of the organic solvent in the recolrding solution is 5 to 40% by weight and preferably 10 to 30% by weight.

Furthermore, as the viscosity modifier added to the recording solution, a generally known one can be used, provided that it does not adversely affect the water-soluble dye, the water-soluble organic solvent or the like. Examples include polyvinyl alcohol, hydroxypropyl cellulose, carboxymethylcellulose, hydroxyethyl cellulose, methyl cellulose, water-soluble acrylic resin, polyvinyl pyrrolidone, gum arabic, dextrin, casein, and heptyne. In containing the viscosity modifier in the recording solution, the content thereof is set to 1 to 15% by weight, preferably 2 to 10% by weight, and more preferably 2 to 8% by weight.

Furthermore, in order to prevent the recording solution from oozing as well as stabilize discharge properties from the nozzle of the ink jet recorder, it is preferable that the surface tension thereof is 30 to 50 dyne/cm (at a liquid temperature of 25° C.) by adding a surface active agent to the recording solution.

The surface active agent added to the recording solution may be any one of nonionic, anionic and cationic surface active agents. When the anionic or cationic surface active agent is added, however, a salt is liable to be deposited. Therefore, the nonionic surface active agent is preferably added.

Examples of the nonionic surface active agent include nonyl phenyl polyethylene glycol ether indicated by a general formula $C_9H_{19}C_6H_4O(CH_2CH_2O)_nH$, octylphenyl polyethylene glycol ether indicated by a general formula $C_8H_{17}C_6H_4O(CH_2CH_2O)_nH$, dodecyl phenyl polyethylene glycol ether indicated by a general formula $C_{12}H_{25}C_6H_4O(CH_2CH_2O)_nH$, a nonionic surface active agent of a hydrocarbon system such as an acetylene glycol ether system indicated by the following chemical formula 1, a nonionic surface active agent of a silicone system such as polyether modified silicone oil indicated by the following chemical formula 2, and a nonionic surface active agent of a fluorine system such as perfluoroalkyl polyoxyethylene ethanol indicated by a general formula $C_nH_{2n+1}O(CH_2CH_2O)_mH$.

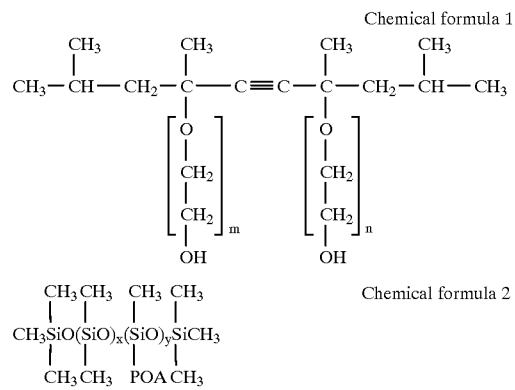

POA is poly oxide alkylene

Examples of the anionic surface active agent include lauryl alcohol sodium sulfuric ester, sodium dodecylbenzenesulfonate, carboxyl modified silicone oil, and perfluoroalkyl potassium carboxylate. Examples of the cationic surface active agent include perfluoroalkyl trialkyl ammonium iodide.

In containing the above-mentioned surface active agent in the recording solution, the surface tension of the recording solution is set to 30 to 50 dyne/cm, and the content of the surface active agent is set to not more than 7% by weight, preferably 0.01 to 5% by weight, more preferably 0.01 to 2% by weight, and still more preferably 0.05 to 1% by weight.

Furthermore, in order to prevent crystals from being deposited in the above-mentioned recording solution, an amphipathic affinity agent is added to the recording solution. Examples of the amphipathic affinity agent include urea, amide, cyclic amide, and alkanolamine. In containing the amphipathic affinity agent in the recording solution, the content thereof is set to not more than 7% by weight, preferably 0.01 to 5% by weight, more preferably 0.01 to 2% by weight, and still more preferably 0.2 to 1% by weight.

When the pH of the recording solution is not less than 8, fungus is further prevented from being produced in the recording solution. Therefore, the pH of the recording solution is set to preferably not less than 8, more preferably in the range of 8 to 11, and still more preferably in the range of 8 to 10 by adding a pH adjustor to the recording solution.

A known pH adjustor generally used can be used as the pH adjustor added to the recording solution, provided that it can control the pH to a desired value without adversely affecting the properties of the recording solution. Examples include amine such as monoethanolamine, diethanolamine, or triethanolamine, an alkali metal hydroxide such as sodium hydroxide, potassium hydroxide, or lithium hydroxide, an alkali metal carbonate such as lithium carbonate, sodium carbonate, or potassium carbonate, an alkali earth metal hydroxide such as calcium hydroxide, sodium tetraborate, and ammonium hydroxide. In adding such the pH adjustor to the recording solution, the pH of the recording solution is set to not less than 8 as described above, so that the content thereof is not more than 4% by weight, preferably 0.01 to 2% by weight, more preferably 0.01 to 1% by weight, and still more preferably 0.1 to 0.3% by weight.

Furthermore, in order to contain metallic ions in the recording solution, a chelating reagent is added to the recording solution. Examples of the chelating reagent include sodium ethylenediaminetetraacetate, ethylenediaminetetraacetic acid, sodium nitrilotriacetate, sodium hydroxyethyl ethylenediamine triacetate, sodium diethylenetriamine pentaacetate, and uramil sodium diacetate. In containing the chelating reagent in the recording solution, the content thereof is set to not more than 4% by weight, preferably 0.01 to 2% by weight, more preferably 0.01 to 1% by weight, and still more preferably 0.1 to 0.5% by weight.

Furthermore, an additive such as an oxygen absorbent such as sodium sulfite or sodium bisulfite, a rust proofing agent such as acid sulfite, sodium thiosulfate, antimony thioglycolate, di-isopropyl ammonium nitrite, pentaerythritol tetranitrate, or dicychlorohexylammonium nitrite, and a quencher such as potassium iodide, potassium bromide, or potassium chloride for preventing the recording solution from fading is added to the above-mentioned recording solution as required. The amount of the additive added to the recording solution is set to not more than 2% by weight and preferably not more than 1% by weight in the case of the oxygen absorbent, to not more than 2% by weight, preferably not more than 1% by weight, and more preferably not more than 0.3% by weight in the case of the rust proofing agent, and to not more than 2% by weight and preferably not more than 1% by weight in the case of the quencher.

Aqueous recording solutions for ink jet in examples of the present invention will be specifically described, and it will be clarified that the aqueous recording solutions for ink jet in the examples are superior in fungus resistance by taking comparative examples.

EXAMPLE 1

In this example, a liquid extracted by squeezing *eichhornia crassipes* and filtering the same was used as a water-soluble fungusproofing agent.

In this example, 89.74% by weight of distilled water, 3.9% by weight of a black dye (PRO-JET FAST BK2 manufactured by Zeneka K.K.), 0.01% by weight of the above-mentioned liquid extracted from *eichhornia crassipes* which is the water-soluble fungusproofing agent, 3.8% by weight of diethylene glycol, 1.5% by weight of ethanol, 0.05% by weight of ethylenediaminetetraacetic acid, and 1.0% by weight of nonyl phenyl polyethylene glycol ether were put in a beaker and were heated, were agitated for one hour while being maintained at 45° C., and were cooled, and were then filtered, to obtain a black aqueous recording solution.

Comparative Example 1

In this comparative example, a black aqueous recording solution was obtained in the same manner as that in the example 1 except that the amount of distilled water was 91.35% by weight, and the amount of diethylene glycol was 2.2% by weight, while the liquid extracted from *eichhorinia crassipes* which is the water-soluble fungusproofing agent was not added.

EXAMPLE 2

In this example, a liquid extracted by squeezing orchidaceae and filtering the same was used as a water-soluble fungusproofing agent.

In this example, 87.0% by weight of distilled water, 3.9% by weight of the same black dye as that in the example 1, 0.3% by weight of the liquid extracted from orchidaceae which is the water-soluble fungusproofing agent, 4.8% by weight of triethylene glycol monobutyl ether, 3.0% by weight of ethanol, 0.3% by weight of sodium ethylenediaminetetraacetate, and 0.7% by weight of polyether modified silicone oil were used, to obtain a black aqueous recording solution in the same manner as that in the example 1.

EXAMPLE 3

In this example, a black aqueous recording solution was obtained in the same manner as that in the example 2 except that the amount of distilled water was 86.6% by weight, while 0.4% by weight of triethanolamine was added.

EXAMPLE 4

In this example, a liquid extracted by squeezing aloe and filtering the same was used as a water-soluble fungusproofing agent.

In this example, 82.6% by weight of distilled water, 4.2% by weight of the same black dye as that in the example 1, 2.7% by weight of the liquid extracted from aloe which is the water-soluble fungusproofing agent, 5.3% by weight of diethylene glycol monobuthyl ether, 4.2% by weight of methanol, 0.4% by weight of sodium diethylenediaminetetraacetate, and 0.6% by weight of octylphenyl polyethylene glycol ether were used, to obtain a black aqueous recording solution in the same manner as that in the example 1.

EXAMPLE 5

In this example, a liquid extracted by squeezing hibiscus and filtering the same was used as a water-soluble fungusproofing agent.

In this example, 80.4% by weight of distilled water, 4.2% by weight of the same black dye as that in the example 1, 4.9% by weight of the liquid extracted from hibiscus which is the water-soluble fungusproofing agent, 5.3% by weight of diethylene glycol monobutyl ether, 4.2% by weight of methanol, 0.4% by weight of sodium ethylenediaminetetraacetate, and 0.6% by weight of octylphenyl polyethylene glycol ether were used, to obtain a black aqueous recording solution in the same manner as that in the example 1.

EXAMPLE 6

In this example, a mixed solution obtained by mixing a liquid extracted by squeezing eichhornia crassipes and filtering the same and a liquid extracted by squeezing orchidaceae and filtering the same in the ratio of 1:1 was used as a water-soluble fungusproofing agent.

In this example, 88.2% by weight of distilled water, 3.9% by weight of the same black dye as that in the example 1, 4.1% by weight of the mixed solution of *eichhornia crassipes* and orchidaceae which is the water-soluble fungusproofing agent, 1.3% by weight of 2-pyrrolidone, 1.5% by weight of ethanol, 0.3% by weight of sodium ethylenediaminetetraacetate, and 0.7% by weight of octylphenyl polyethylene glycol ether were used, to obtain a black aqueous recording solution in the same manner as that in the example 1.

EXAMPLE 7

In this example, the same liquid extracted from hibiscus as that in the example 5 was used as a water-soluble fungusproofing agent, and 81.8% by weight of distilled water, 3.9% by weight of the same black dye as that in the example 1, 5.7% by weight of the liquid extracted from hibiscus which is the water-soluble fungusproofing agent, 1.3% by weight of 2-pyrrolidone, 1.5% by weight of ethanol, 0.3% by weight of sodium ethylendiaminetetraacetate, and 0.7% by weight of octylphenyl polyethylene glycol ether were used, to obtain a black aqueous recording solution in the same manner as that in the example 1.

EXAMPLE 8

In this example, the same liquid extracted from *eichhornia crassipes* as that in the example 1 was used as a water-soluble fungusproofing agent, and 87.9% by weight of distilled water, 3.0% by weight of a blue dye (PRO-JET FAST CY2 manufactured by Zeneka K.K.), 0.3% by weight of the liquid extracted from *eichhornia crassipes* which is the water-soluble fungusproofing agent, 4.8% by weight of triethylene glycol monobutyl ether, 3.0% by weight of ethanol, 0.3% by weight of sodium ethylenediaminetetraacetate, and 0.7% by weight of polyether modified silicone oil were used, to obtain a blue aqueous recording solution in the same manner as that in the example 1.

EXAMPLE 9

In this example, a blue aqueous recording solution was obtained in the same manner as that in the example 8 except that the amount of distilled water was 87.5% by weight, while 0.4% by weight of triethanolamine was added.

EXAMPLE 10

In this example, the same liquid extracted from orchidaceae as that in the example 2 was used as a water-soluble fungusproofing agent, and 84.3% by weight of distilled water, 2.5% by weight of a red dye (Aizen Acid Red 52 manufactured by Hodogaya Kagaku K.K.), 2.7% by weight of the liquid extracted from orchidaceae which is the water-soluble fungusproofing agent, 5.3% by weight of diethylene glycol monobuthyl ether, 4.2% by weight of methanol, 0.4% by weight of sodium ethylenediaminetetraacetate, and 0.6% by weight of octylphenyl polyethylene ether were used, to obtain a red aqueous recording solution in the same manner as that in the example 1.

EXAMPLE 11

In this example, the same liquid extracted from hibiscus as that in the example 5 was used as a water-soluble fungusproofing agent, and 82.1% by weight of distilled water, 2.5% by weight of the same red dye as that in the exempt 10, 4.9% by weight of the liquid extracted from hibiscus which is the water-soluble fungusproofing agent, 5.3% by weight of diethylene glycol monobuthyl ether, 4.2% by weight of methanol, 0.4% by weight of sodium ethylenediaminetetraacetate, and 0.6% by weight of octylphenyl polyethylene glycol ether were used, to obtain a red aqueous recording solution in the same manner as that in the example 1.

EXAMPLE 12

In this example, the same liquid extracted from aloe as that in the example 4 was used as a water-soluble fungusproofing agent, and 90.5% by weight of distilled water, 2.7% by weight of a yellow dye (BAYSORIPT YELLOW CA 51092 manufactured by Bayer K.K.), 3.0% by weight of the liquid extracted from aloe which is the water-soluble fungusproofing agent, 1.3% by weight of 2-pyrrolidone, 1.5% by weight of ethanol, 0.3% by weight of sodium ethylenediaminetetraacetate, and 0.7% by weight of octylphenyl polyethylene glycol ether were used, to obtain a yellow aqueous recording solution in the same manner as that in the example 1.

EXAMPLE 13

In this example, a yellow aqueous recording solution was obtained in the same manner as that in the example 12 except that the amount of distilled water was 87.6% by weight, while the amount of the liquid extracted from aloe which is the water-soluble fungusproofing agent was 5.9% by weight.

With respect to each of the aqueous recording solutions in the examples 1 to 13 and in the comparative example 1 obtained in the above-mentioned manner, the fungus resistance of the aqueous recording solution was examined in conformity to a method of test for fungus resistance of JIS Z 2911 defined in Japanese Industrial Standard (JIS). Further, a square solid image measuring 5×5 mm was printed on paper using the aqueous recording solution, and its printing surface was rubbed by a urethane rubber blade after 30 seconds, to examine the fixing properties of the aqueous recording solution. The results were shown in the following Table 1. In the following Table 1, with respect to the fungus resistance, a case where no fungus was produced is indicated by ⊚, a case where fungus was hardly produced is indicated by ○, and a case where fungus was produced is indicated by X. Further, with respect to the fixing properties, a case where there was no tailing from a printing portion to a white portion is indicated by ○, and a case where there occurred tailing is indicated by X.

TABLE 1

|  | EXAMPLE | | | | | | | | | | | | | COMPARATIVE EXAMPLE |
|---|---|---|---|---|---|---|---|---|---|---|---|---|---|---|
|  | 1 | 2 | 3 | 4 | 5 | 6 | 7 | 8 | 9 | 10 | 11 | 12 | 13 | 1 |
| FUNGUS RESISTANCE | ○ | ○ | ◎ | ○ | ○ | ○ | ○ | ○ | ◎ | ○ | ○ | ○ | ○ | X |
| FIXING PROPERTIES | ○ | ○ | ○ | ○ | ○ | ○ | X | ○ | ○ | ○ | ○ | ○ | X | ○ |

As a result, in the aqueous recording solution in the comparative example 1 in which no water-soluble fungusproofing agent composed of a liquid extracted from at least one type of malvaceae, orchidaceae and aloe was added, fungus was produced. On the other hand, in the aqueous recording solution in the examples to which the water-soluble fungusproofing agent was added, no fungus was produced. Particularly in the aqueous recording solutions in the example 3 and in the example 9 to which triethanolamine was added, no fungus was produced. When the aqueous recording solution was used in an ink jet recorder such as an ink jet printer, a solution passage and a nozzle in the recorder were not clogged, and the color of the aqueous recording solution was not changed due to the action of the fungus.

Furthermore, in the aqueous recording solutions in the example 7 and the example 13 in which the content of the liquid extracted from at least one type of malvaceae, orchidaceae and aloe as an aqueous fungusproofing agent was more than 5% by weight, tailing occurred in the test of the fixing properties, so that the fixing properties were degraded. On the other hand, in the aqueous recording solutions in the examples 1 to 6 and in the examples 8 to 12 in which the content of the extracted liquid was in the range of 0.01 to 5% by weight, no tailing occurred, so that good fixing properties were exhibited.

EXAMPLE 14

In this example, 91.34% by weight of distilled water, 3.9% by weight of a black dye (PRO-JET FAST BK2 manufactured by Zeneka K.K.), 0.01% by weight of sodium silicate which is a water-soluble fungusproofing agent, 2.2% by weight of diethylene glycol, 1.5% by weight of ethanol, 0.05% by weight of ethylenediaminetetraacetic acid, and 1.0% by weight of nonyl phenyl polyethylene glycol ether were put in a beaker and were heated, were agitated for one hour while being maintained at 45° C., and were cooled, and were then filtered, to obtain a black aqueous recording solution.

Comparative Example 2

In this comparative example, a black aqueous recording solution was obtained in the same manner as the above-mentioned example 14 except that the amount of distilled water was 91.35% by weight, while the alkali silicate which is the water-soluble fungusproofing agent was not added.

EXAMPLE 15

In this example, 87.1% by weight of distilled water, 3.9% by weight of the same black dye as that in the example 14, 0.2% by weight of potassium silicate which is a water-soluble fungusproofing agent, 4.8% by weight of triethylene glycol monobutyl ether, 3.0% by weight of ethanol, 0.3% by weight of sodium ethylenediamineacetate, and 0.7% by weight of polyether modified silicone oil were used, to obtain a black aqueous recording solution in the same manner as that in the example 14.

EXAMPLE 16

In this example, a black aqueous recording solution was obtained in the same manner as that in the example 15 except that the amount of distilled water was 86.7% by weight, while 0.4% by weight of triethanolamine was added.

EXAMPLE 17

In this example, 83.6% by weight of distilled water, 4.2% by weight of the same black dye as that in the example 14, 2.7% by weight of potassium silicate which is a water-soluble fungusproofing agent, 5.3% by weight of diethylene glycol monobuthyl ether, 3.2% by weight of methanol, 0.4% by weight of sodium ethylenediaminetetraacetate, and 0.6% by weight of octylphenyl polyethylene glycol ether were used, to obtain a black aqueous recording solution in the same manner as that in the example 14.

EXAMPLE 18

In this example, 81.4% by weight of distilled water, 4.2% by weight of the same black dye as that in the example 14, 4.9% by weight of potassium silicate which is a water-soluble fungusproofing agent, 5.3% by weight of diethylene glycol monobuthyl ether, 3.2% by weight of methanol, 0.4% by weight of sodium ethylenediaminetetraacetate, and 0.6% by weight of octylphenyl polyethylene glycol ether were used, to obtain a black aqueous recording solution in the same manner as that in the example 14.

EXAMPLE 19

In this example, 82.6% by weight of distilled water, 3.9% by weight of the same black dye as that in the example 14, 9.7% by weight of sodium silicate which is a water-soluble fungusproofing agent, 1.3% by weight of 2-pyrrolidone, 1.5% by weight of ethanol, 0.3% by weight of sodium ethylenediaminetetraacetate, and 0.7% by weight of octylphenyl polyethylene glycol ether were used, to obtain a black aqueous recording solution in the same manner as that in the example 14.

EXAMPLE 20

In this example, 81.8% by weight of distilled water, 3.9% by weight of the same black dye as that in the example 14, 10.5% by weight of potassium silicate which is a water-soluble fungusproofing agent, 1.3% by weight of 2-pyrrolidone, 1.5% by weight of ethanol, 0.3% by weight of sodium ethylenediaminetetraacetate, and 0.7% by weight of octylphenyl polyethylene glycol ether were used, to obtain a black aqueous recording solution in the same manner as that in the example 14.

EXAMPLE 21

In this example, 91.34% by weight of distilled ether, 3.9% by weight of a black dye (Basacid BK X38 manufactured by BASF K.K.), 0.01% by weight of sodium silicate which is a water-soluble fungusproofing agent, 2.2% by weight of diethylene glycol, 1.5% by weight of ethanol, 0.05% by weight of sodium ethylenediaminetetraacetate, and 1.0% by weight of nonyl phenyl polyethylene glycol ether were used, to obtain a black aqueous recording solution in the same manner as that in the example 14.

Comparative Example 3

In this comparative example, a black aqueous recording solution was obtained in the same manner as that in the above-mentioned example 21 except that the amount of distilled water was 91.35% by weight, while the alkali silicate which is the water-soluble fungusproofing agent was not added.

EXAMPLE 22

In this example, 87.1% by weight of distilled water, 3.9% by weight of a cyan dye (JET FAST CY2 manufactured by Zeneka K.K.), 0.2% by weight of potassium silicate which is a water-soluble fungusproofing agent, 4.8% by weight of triethylene glycol monobutyl ether, 3.0% by weight of ethanol, 0.3% by weight of sodium ethylenediaminetetraacetate, and 0.7% by weight of polyether modified silicone oil were used, to obtain a cyan ink in the same manner as that in the example 14.

EXAMPLE 23

In this example, a cyan ink was obtained in the same manner as that in the above-mentioned example 22 except that the amount of distilled water was 86.7% by weight, while 0.4% by weight of triethanolamine was added.

EXAMPLE 24

In this example, 83.6% by weight of distilled water, 4.2% by weight of a magenta dye (AIZEN Acid Red 52 manufactured by Hodogaya Kagaku K. K.), 2.7% by weight of potassium silicate which is a water-soluble fungusproofing agent, 5.3% by weight of diethylene glycol monobuthyl ether, 3.2% by weight of methanol, 0.4% by weight of sodium ethylenediaminetetraacetate, and 0.6% by weight of octylphenyl polyethylene glycol ether were used, to obtain a magenta aqueous recording solution in the same manner as that in the example 14.

EXAMPLE 25

In this example, 81.4% by weight of distilled water, 4.2% by weight of the same magenta dye as that in the example 24, 4.9% by weight of sodium silicate which is a water-soluble fungusproofing agent, 5.3% by weight of diethylene glycol monobuthyl ether, 3.2% by weight of methanol, 0.4% by weight of sodium ethylenediaminetetraacetate, and 0.6% by weight of octylphenyl polyethylene glycol ether were used, to obtain a magenta aqueous recording solution in the same manner as that in the example 14.

EXAMPLE 26

In this example, 82.6% by weight of distilled water, 3.9% by weight of a yellow dye (BAYSORIPT YELLOW CA 51092 manufactured by Bayer K.K.), 9.7% by weight of sodium silicate which is a water-soluble fungusproofing agent, 1.3% by weight of 2-pyrrolidone, 1.5% by weight of ethanol, 0.3% by weight of sodium ethylenediaminetetraacetate, and 0.7% by weight of octylphenyl polyethylene glycol ether were used, to obtain a yellow aqueous recording solution in the same manner as that in the example 14.

EXAMPLE 27

In this example, 81.8% by weight of distilled water, 3.9% by weight of the same yellow dye as that in the example 26, 10.5% by weight of potassium silicate which is a water-soluble fungusproofing agent, 1.3% by weight of 2-pyrrolidone, 1.5% by weight of ethanol, 0.3% by weight of sodium ethylenediaminetetraacetate, and 0.7% by weight of octylphenyl polyethylene glycol ether were used, to obtain a yellow aqueous recording solution in the same manner as that in the example 14.

With respect to each of the aqueous recording solutions in the examples 14 to 27 and in the comparative examples 2 and 3 obtained in the above-mentioned manner, the fungus resistance of the aqueous recording solution was examined in conformity to a method of test for fungus resistance of JIS Z 2911 defined in Japanese Industrial Standard (JIS). Further, a square solid image measuring 5×5 mm was further printed on paper using the aqueous recording solution, and its printing surface was rubbed by a urethane rubber blade after 30 seconds, to examine the fixing properties of the aqueous recording solution. The results were shown in the following Table 2. In the following Table 2, with respect to the fungus resistance, a case where no fungus was produced is indicated by ⊚, a case where fungus was hardly produced is indicated by ○, and a case where fungus was produced is indicated by X. Further, with respect to the fixing properties, a case where there was no tailing from a printing portion to a white portion is indicated by ○, and a case where there occurred tailing is indicated by X.

TABLE 2

| | EXAMPLE | | | | | | | | | |
|---|---|---|---|---|---|---|---|---|---|---|
| | 14 | 15 | 16 | 17 | 18 | 19 | 20 | 21 | 22 | 23 |
| pH | 8.0 | 8.0 | 8.0 | 8.0 | 8.0 | 8.0 | 8.0 | 8.0 | 8.0 | 8.0 |
| FUNGUS RESISTANCE | ○ | ○ | ⊚ | ○ | ○ | ○ | ○ | ○ | ○ | ⊚ |
| FIXING PROPERTIES | ○ | ○ | ○ | ○ | ○ | ○ | X | ○ | ○ | ○ |

| | EXAMPLE | | | | COMPARATIVE EXAMPLE | |
|---|---|---|---|---|---|---|
| | 24 | 25 | 26 | 27 | 2 | 3 |
| pH | 8.0 | 8.0 | 8.0 | 8.0 | 8.0 | 8.0 |
| FUNGUS RESISTANCE | ○ | ○ | ○ | ○ | X | X |
| FIXING PROPERTIES | ○ | ○ | ○ | X | ○ | ○ |

As a result, in the aqueous recording solutions in the comparative examples 2 and 3 in which no alkali silicate which is a water-soluble fungusproofing agent was added, fungus was produced. On the other hand, in the aqueous recording solutions in the examples to which the water-soluble fungusproofing agent composed of alkali silicate indicated by the foregoing general formula (1) was added, no fungus was produced. Particularly in the aqueous recording solutions in the example 16 and in the example 23 to which triethanolamine was added, no fungus was produced. When the aqueous recording solution was used in an ink jet recorder such as an ink jet printer, a solution passage and a nozzle in the recorder were not clogged, and the color of the aqueous recording solution was not changed due to the action of the fungus.

Furthermore, in the aqueous recording solutions in the examples 20 and 27 in which the content of alkali silicate which is a water-soluble fungusproofing agent was not less than 10% by weight, tailing occurred in the test of the fixing properties, so that the fixing properties were degraded. On the other hand, in the aqueous recording solutions in the examples 14 to 19 and in the examples 21 to 26 in which the content of the alkali silicate was in the range of 0.01 to 10% by weight, no tailing occurred, so that good fixing properties were exhibited.

Although the present invention has been fully described by way of examples, it is to be noted that various changes and modification will be apparent to those skilled in the art.

Therefore, unless otherwise such changes and modifications depart from the scope of the present invention, they should be construed as being included therein.

What is claimed is:

1. An aqueous recording solution for ink jet containing a coloring agent, a water-soluble fungusproofiig agent and water, wherein the water-soluble firngusproofing agent is a liquid extracted from at least one plant selected from the group consisting of nialvaccae, orclidaceac and aloe, said coloring agent is selected from the group consisting of pigment, oil-soluble dye and water-soluble dye, said fiingusproofing, agent is present in the aqueous recording solution in an amount from 0.01 to 5% by weight, and said coloring agent is present in the aqueous recording solution in an amount from 0.5 to 10% by weight.

2. The aqueous recording solution for ink jet according to claim 1, wherein said aqueous recording solution contains at least one water-soluble organic solvent selected from the group consisting of monohydroxy alcohol, polyhydroxy alcohol, polyhydroxy alcohol alkyl ether and cyclic amide, said organic solvent is present in the aqueous recording solution in an amount from 5 to 40% by weight.

3. The aqueous recording solution for ink jet according to claim 2, wherein said monohydroxy alcohol is present in the aqueous recording solution in an amount of not more than 10% by weight.

4. The aqueous recording solution for ink jet according to claim 2, wherein said polyhydroxy alcohol is present in the aqueous recording solution in an amount from 5 to 30% by weight.

5. The aqueous recording solution for ink jet according to claim 2, wherein said polyhydroxy alcohol alkyl ether is present in the aqueous recording solution in an amount from 5 to 20% by weight.

6. The aqueous recording solution for ink jet according to claim 2, wherein said cyclic amide is present in the aqueous recording solution in an amount of not more than 10% by weight.

7. The aqueous recording solution for ink jet according to claim 2, wherein said aqueous recording solution further contains a nonionic surface active agent in an amount in the aqueous recording solution of not more than 7% by weight.

8. The aqueous recording solution for ink jet according to claim 7, wherein said aqueous recording solution contains at least one amphipathic affinity agent selected from the group consisting of urea and alkanol amine in an amount in the recording solution of not more than 7% by weight.

9. The aqueous recording solution for ink jet according to claim 8, wherein said aqueous recording solution contains at least one additive selected from the group consisting of a pH adjustor and a chelating agent, said pH adjustor selected from the group consisting of amine, alkali metal hydroxide, alkali metal carbonate, alkali earth metal hydroxide, sodium tetraborate and ammonium hydroxide, said chelating agent selected from the group consisting of sodium ethylenediaminetetraacetate, ethylenediaminetetraacetic acid, sodium nitrilotriacetate, sodium hydroxvethvl ethylenediaminetetraacetate, sodium diethylenetriamine pentaacetate and uramil sodium diacetate, in an amount in the aqueous recording solution of not more than 4% by weight.

10. The aqueous recording solution for ink jet according to claim 1, wherein a pH of said aqueous recording solution is not less than 8, and a surface tension of said aqueous recording solution at a temperature of 25° C. is 30 to 50 dyne/cm.

11. An aqueous recording solution for ink jet containing a coloring agent, a water-soluble fungusproofing agent and water, wherein the water-soluble fungusproofing agent is $M_2O \cdot nSiO_2$ (M is K or Na, and n is an integer of 1 to 4), said coloring agent is selected from the group consisting of pigment, oil-soluble dye and water-soluble dye, said fungusproofing agent is present in the aqueous recording solution in an amount from 0.01 to 10% by weight, and said coloring agent is present in the aqueous recording solution in an amount from 0.5 to 10% by weight.

12. The aqueous recording solution for ink jet according to claim 11, wherein said fungusproofing agent is present in the aqueous recording solution in an amount from 0.1 to 4.5% by weight.

13. The aqueous recording solution for ink jet according to claim 11, wherein said recording solution contains at least one water-soluble organic solvent selected from the group consisting of monohydroxy alcohol, polyhydroxy alcohol, polyhydroxy alcohol alkyl ether and cyclic amide, said water-soluble organic solvent is present in the aqueous recording solution in an amount from 5 to 40% by weight.

14. The aqueous recording solution for ink jet according to claim 13, wherein said monohydroxy alcohol is present in the aqueous recording solution in an amount of not more than 10% by weight.

15. The aqueous recording solutiordfor ink jet according to claim 13, wherein said polyhydroxy alcohol is present in the aqueous recording solution in amount from 5 to 30% by weight.

16. The aqueous recording solution for ink jet according to claim 13, wherein said polyhydroxy alcohol alkyl ether is present in the aqueous recording solution in an amount from 5 to 20% by weight.

17. The aqueous recording solution for ink jet according to claim 13, wherein said cyclic amide is present in the aqueous recording solution in an amount of not more than 10% by weight.

18. The aqueous recording solution for ink jet according to claim 13, wherein said recording solution further contains a non-ionic surface active agent, in an amount in the aqueous recording solution of not more than 7% by weight.

19. The aqueous recording solution for ink jet according to claim 18, wherein said aqueous recording solution further contains at least one amphipathic affinity agent selected from the group consisting of urea and alkanol amine, said at least one amphipathic affinity agent is present in the recording solution in an amount of not more than 7% by weight.

20. The aqueous recording solution for ink jet according to claim 18, wherein said aqueous recording solution contains at least one additive selected from the group consisting of a pH adjustor and a chelating agent, said pH adjustor selected from the group consisting of amine, alkali metal hydroxide, alkali metal carbonate, alkali earth metal hydroxide, sodium tetraborate and ammonium hydroxide, said chelating agent selected from the group consisting of sodium ethylenediaminetetraacetate, ethylenediaminetetraacetic acid, sodium nitrilotriacetate, sodium hydroxvethyl ethylenediaminetetraacetate, sodium diethylenetriamine pentaacetate and uramil sodium diacetate, in an amount in the aqueous recording solution of not more than 4% by weight.

21. The aqueous recording solution for ink jet according to claim 14, wherein a pH of said aqueous recording solution is not less than 8, and a surface tension of said aqueous recording solution at a temperature of 25° C. is 30 to 50 dyne/cm.

22. An aqueous recording solution for ink jet containing a coloring agent, a water-soluble fungusproofing agent, a water-soluble organic solvent and water, wherein the water-soluble ftngusproofing agent is a liquid extracted from at least one plant selected from the group consisting of malvaceae, orchidaccae and aloe, said water-soluble fungusproofing agent is present in the aqueous recording solution in an amount from 0.01 to 5% by weight, said coloring agent selected from the group consisting of pigment, oil-soluble dye and water-soluble dye, said organic solvent being present in the recording solution in an amount from 5 to 40% by weight, and said coloring agent is present in the aqueous recording solution in an amount from 0.5 to 10% by weight.

23. An aqueous recording solution for ink jet containing a coloring agent, a water-soluble fungusproofing agent, a water-soluble organic solvent and water, wherein the water-soluble fungusproofing agent is $M_2O \cdot nSiO_2$ (M is K or Na, and n is an integer of 1 to 4), said water-soluble fungusproofing agent is present in the aqueous recording solution in an amount from 0.01 to 10% by weight, said coloring agent selected from the group consisting of pigment, oil-soluble dye and water-soluble dye, said organic solvent being present in the recording solution in an amount from 5 to 40% by weight, and said coloring agent is present in the aqueous recording solution in an amount from 0.5 to 10% by weight.

* * * * *

UNITED STATES PATENT AND TRADEMARK OFFICE
CERTIFICATE OF CORRECTION

PATENT NO. : 5,919,291
DATED : July 6, 1999
INVENTOR(S) : Hotomi et al.

It is certified that error appears in the above-identified patent and that said Letters Patent is hereby corrected as shown below:

In the claims:

Claim 1, line 23, change "fungusproofiiig" to --fungusproofing--;
   line 25, change "firngusproofing" to --fungusproofing--;
   line 27, change "nialvaccae, orclidaceac" to --malvaceae, orchidaceae--; and
   line 30, change "fiingusproofing" to --fungusproofing--.

Claim 9, line 8, change "8" to --7--; and
   line 17, change "hydroxvethvl" to --hydroxyethyl--.

Claim 11, line 31, change "M₂O.nSiO₂" to --M₂O·nSiO₂--.

Claim 15, line 59, change "solutiordfor" to --solution for--.

Claim 21, line 37, change "14" to --11--.

Claim 22, line 9, change "ftngusproofing" to --fungusproofing--; and
   line 11, change "orchidaccae" to --orchidaceae--.

Claim 23, line 25, change "M₂O.nSiO₂" to M₂O·nSiO₂--.

Signed and Sealed this

Thirtieth Day of November, 1999

*Attest:*

*Attesting Officer*

Q. TODD DICKINSON

*Acting Commissioner of Patents and Trademarks*